(12) United States Patent
Davis et al.

(10) Patent No.: US 7,711,433 B2
(45) Date of Patent: May 4, 2010

(54) SWITCHED POWER USING TELEMETRY IN AN IMPLANTABLE MEDICAL DEVICE

(75) Inventors: Timothy J. Davis, Coon Rapids, MN (US); Leroy L. Perz, Buffalo, MN (US); Nathan A. Torgerson, Andover, MN (US); Carl D. Wahlstrand, Lino Lakes, MN (US); David W. Hoffman, Inver Grove Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 603 days.

(21) Appl. No.: 11/185,526

(22) Filed: Jul. 20, 2005

(65) Prior Publication Data

US 2006/0020307 A1 Jan. 26, 2006

Related U.S. Application Data

(60) Provisional application No. 60/589,950, filed on Jul. 21, 2004, provisional application No. 60/589,393, filed on Jul. 20, 2004.

(51) Int. Cl.
 *A61N 1/378* (2006.01)
(52) U.S. Cl. ...................................................... 607/60
(58) Field of Classification Search .................. 607/60, 607/61; 128/903
 See application file for complete search history.

(56) References Cited

U.S. PATENT DOCUMENTS

| 3,357,434 A | 12/1967 | Abell |
| 3,888,260 A | 6/1975 | Fischell |
| 4,071,032 A | 1/1978 | Schulman |
| 4,102,344 A * | 7/1978 | Conway et al. ............... 607/17 |
| 4,134,408 A | 1/1979 | Brownlee et al. |
| 4,186,749 A | 2/1980 | Fryer |
| 4,373,527 A | 2/1983 | Fischell et al. |
| 5,113,869 A | 5/1992 | Nappholz et al. |
| 5,279,292 A | 1/1994 | Baumann et al. |
| 5,314,453 A | 5/1994 | Jeutter |
| 5,314,457 A | 5/1994 | Jeutter et al. |
| 5,358,514 A * | 10/1994 | Schulman et al. ............. 607/61 |
| 5,411,537 A | 5/1995 | Munshi et al. |
| 5,613,935 A | 3/1997 | Jarvik |

(Continued)

FOREIGN PATENT DOCUMENTS

EP 0 472 411 2/1992

(Continued)

OTHER PUBLICATIONS

Medtronic, Inc. "Mattrix Neurostimulation System", Brochure, 1995.

(Continued)

*Primary Examiner*—Carl H Layno
*Assistant Examiner*—Brian T Gedeon
(74) *Attorney, Agent, or Firm*—IPLM Group, P.A.

(57) ABSTRACT

A system, method and implantable medical for providing switched power while providing transcutaneous telemetry communication with an implanted medical device having an internal power source. An electronics module is adapted to supply the therapeutic output to the patient. A telemetry module is configured for transcutaneous telemetry communication. The telemetry module obtains power from the telemetry signal during transcutaneous telemetry communication.

48 Claims, 10 Drawing Sheets

U.S. PATENT DOCUMENTS

| | | | |
|---|---|---|---|
| 5,690,693 | A | 11/1997 | Wang et al. |
| 5,713,939 | A * | 2/1998 | Nedungadi et al. ............. 607/33 |
| 5,733,313 | A | 3/1998 | Barreras, Sr. et al. |
| 5,938,691 | A | 8/1999 | Schulman et al. |
| 5,991,664 | A | 11/1999 | Seligman |
| 6,067,474 | A | 5/2000 | Schulman et al. |
| 6,154,677 | A | 11/2000 | Leysieffer |
| 6,275,737 | B1 | 8/2001 | Mann |
| 6,308,101 | B1 | 10/2001 | Faltys et al. |
| 6,324,430 | B1 | 11/2001 | Zarinetchi et al. |
| 6,505,077 | B1 | 1/2003 | Kast et al. |
| 6,516,227 | B1 | 2/2003 | Meadows et al. |
| 6,631,296 | B1 * | 10/2003 | Parramon et al. ............. 607/61 |
| 6,682,480 | B1 * | 1/2004 | Habib et al. ................ 600/300 |
| 6,699,187 | B2 | 3/2004 | Webb et al. |
| 6,985,773 | B2 * | 1/2006 | Von Arx et al. ............... 607/32 |
| 2001/0037366 | A1 | 11/2001 | Webb et al. |
| 2003/0065370 | A1 | 4/2003 | Lebel et al. |
| 2003/0139783 | A1 | 7/2003 | Kilgore et al. |
| 2003/0149459 | A1 | 8/2003 | Von Arx et al. |
| 2004/0059392 | A1 | 3/2004 | Parramon et al. |
| 2004/0176822 | A1 * | 9/2004 | Thompson et al. ............ 607/60 |

FOREIGN PATENT DOCUMENTS

| | | |
|---|---|---|
| EP | 1 048 324 | 11/2000 |
| WO | WO 98/37926 | 9/1998 |
| WO | WO 99/06108 | 2/1999 |
| WO | WO 99/44684 | 9/1999 |
| WO | WO 00/01442 | 1/2000 |
| WO | WO 01/83029 | 11/2001 |
| WO | WO 01/97908 | 12/2001 |
| WO | WO 03/033070 | 4/2003 |

OTHER PUBLICATIONS

Medtronic, Inc. "Implantable Neurostimulation Systems", 1998.

* cited by examiner

SWITCHED POWER USING TELEMETRY IN AN IMPLANTABLE MEDICAL DEVICE

RELATED APPLICATION

This application claims priority to provisional U.S. Application Ser. No. 60/589,393, filed Jul. 20, 2004, and provisional U.S. Application Ser. No. 60/589,950, filed Jul. 21, 2004.

FIELD OF THE INVENTION

The present invention relates generally to implantable medical devices and, more particularly, to implantable medical devices providing a therapeutic electrical output and transcutaneous telemetry.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Some of these devices, if not all, and other devices either provide an electrical output or otherwise contain electrical circuitry to perform their intended function.

It is common for implantable medical devices, including implantable medical devices providing an electrical therapeutic output, to utilize transcutaneous telemetry to transfer information to and from the implanted medical device. Information typically transferred to an implanted medical device includes transferring instructions or programs to the implanted medical device from an external device such as an external programmer. Information typically transferred from an implanted medical includes information regarding the status and/or performance of the implanted medical device.

Typical telemetry communication involves analog electrical components which sometimes operate at greater voltages and/or greater currents than digital circuits. Thus, telemetry modules and associated circuitry often provide a significant drain on power resources of implantable medical devices.

BRIEF SUMMARY OF THE INVENTION

Since implantable medical devices typically are constrained in physical size, longevity or both, conservation of internal power resources is of great importance.

An embodiment of the present invention powers at least some of the internal components of the implanted medical device using power derived from the telemetry signal transmitted by an external device such as is commonly used to control and/or program such implanted medical device.

By using power from the external programmer/controller during telemetry, precious internal power, typically supplied by an internal battery, may be conserved.

In an embodiment of the invention, the voltage derived from the received telemetry transmission is monitored. If the voltage is greater than the voltage available from the internal power source of the implanted medical device, power from the telemetry signal is delivered to at least some components of the implanted medical devices, such as components of the telemetry section on the implanted medical device. When the voltage available from the telemetry signal is lower than the voltage available from the internal power source, then power is switched back to the internal power source.

Using the voltage on the antenna to raise the supply voltage on the receiver allows the user to communicate in a noisy environment by increasing the downlink strength to levels above the noise floor of the receiver.

In an embodiment, the present invention provides an implantable medical device for providing a therapeutic output to a patient and configured for transcutaneous telemetry communication with an external device via a telemetry signal. An electronics module is adapted to supply the therapeutic output to the patient. A telemetry module is configured for the transcutaneous telemetry communication. The telemetry module obtaining power from the telemetry signal during transcutaneous telemetry communication.

In an alternative embodiment, the present invention provides a system for providing a therapeutic output to a patient having an external device configured for transcutaneous telemetry communication with the implantable medical device and the implantable medical device described above.

In an alternative embodiment, the present invention provides an implantable medical device for providing a therapeutic output to a patient, configured for transcutaneous telemetry communication with an external device. An electronics module is adapted to supply the therapeutic output to the patient. A telemetry module is configured for transcutaneous telemetry communication using a telemetry signal. A switching module, operatively coupled to the power source and the telemetry module, provides power for the telemetry module from the telemetry signal when the telemetry signal is available.

In an alternative embodiment, the present invention provides a system for providing a therapeutic output to a patient having an external device configured for transcutaneous telemetry communication with the implantable medical device and an implantable medical device as described above.

In an alternative embodiment, the present invention provides a method of providing transcutaneous telemetry communication with an implanted medical device having an internal power source. Transcutaneous telemetry communication is provided with a telemetry module of the implanted medical device using a telemetry signal. Power is supplied to the telemetry module in the implanted medical device with the internal power source when the telemetry signal is not available. Power is supplied to the telemetry module in the implanted medical device with the telemetry signal when the telemetry signal is available.

In a preferred embodiment, the telemetry module relies upon power from the telemetry signal to supplement power from the internal power source.

In a preferred embodiment, the telemetry module obtains power from one of an internal power source and the telemetry signal.

In a preferred embodiment, the telemetry module obtains power from the telemetry signal instead of from the internal power source when the telemetry signal is available.

In a preferred embodiment, the telemetry module always obtains power from the telemetry signal instead of from the internal power source whenever the telemetry signal is available.

In a preferred embodiment, the telemetry module obtains power from the telemetry signal whenever energy from the telemetry signal is sufficient to power the telemetry module.

In a preferred embodiment, the telemetry module obtains power from the telemetry signal instead of the internal power source whenever energy from the telemetry signal is sufficient to power the telemetry module.

DETAILED DESCRIPTION OF THE INVENTION

Embodiments of the present invention have usefulness in many different implantable medical devices. A preferred embodiment of the present invention is especially useful in an implantable medical device providing electrical stimulation therapy. An example of such a device, system and method is described in U.S. Pat. No. 6,505,077, Kast et al, Implantable Medical Device With External Recharging Coil Electrical Connection, the content of which are hereby incorporated by reference.

Figure 1:
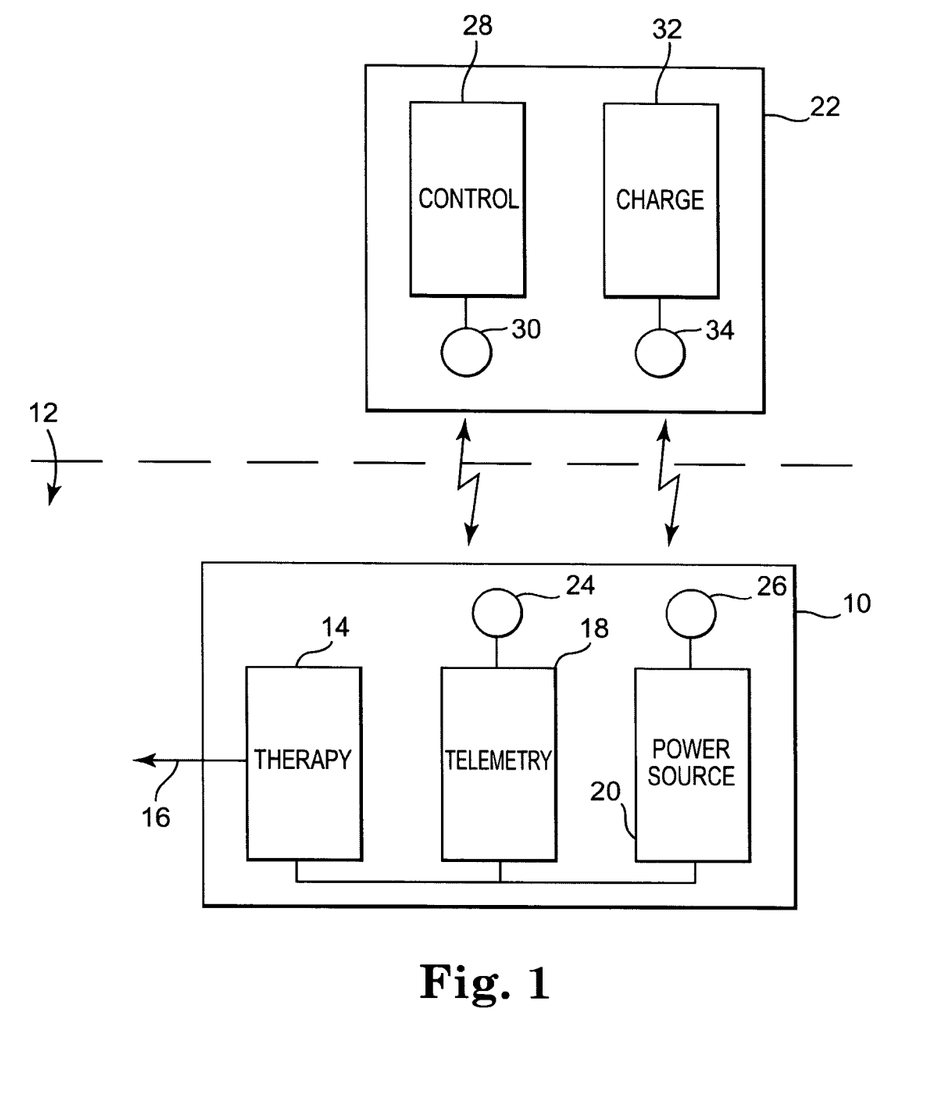
FIG. 1 is a block diagram of an implantable medical device used in conjunction with an external device.

A close-up diagrammatic view of implantable medical device 10 implanted into patient 12 is illustrated in FIG. 1. Implantable medical device 10 is generally composed of therapy module 14 which provides a therapeutic output 16 to patient 12, telemetry module 18 and power supply 20 providing electrical power to both therapy module 14 and telemetry module 18. In general, implantable medical device may by any of a variety of commonly available implantable medical devices providing a therapeutic output 16 to a patient 12. Examples, of such devices include, but are not limited to, implantable neurostimulators, drug pumps, cardiac pacemakers and defibrillators and other devices. Therapy modules 14 associated with such implantable medical devices 10 are well known in the industry.

Telemetry module 18 may be any of a variety of commonly known and available modules for supporting transcutaneous communication between implantable medical device 10 and external device 22 which is generally used for controlling or programming implantable medical device 10 or for providing information regarding the condition, state, status or history of implantable medical device 10 or information relating to patient 12. Telemetry techniques are commonly known in the industry and typically involve the transmission and reception of an electromagnetic wave between implantable medical device 10 and external device 22. Any of a number of commonly available telemetry schemes may be utilized.

Power source 20 may be any of a variety of commonly known and available power supply such as chemical batteries and, in particular, rechargeable batteries. Power source 20 may provide electrical power to both therapy module 14 and telemetry module 18 although it is to be recognized and understood that therapy module 14 and telemetry module 18 may have their own separate power sources.

Telemetry antenna 24, coupled to telemetry module 18, is adapted to receive electromagnetic signals sent transcutaneously from external device 22 and to transmit electromagnetic signals toward external device 22.

Power antenna 26, coupled to power source 20, is adapted to receive electromagnetic energy from external device 22 for the purpose of supplying energy to implantable medical device 10, including, but not limited to, recharging of power source 20.

While shown separately, telemetry antenna 24 may be nested with power antenna 26 or, in an alternative embodiment, telemetry antenna 24 may be combined with power antenna 26.

External device 22 contains control module 28 which is coupled to telemetry antenna 30 and is adapted to either control or program implantable medical device 10 or provide information about implantable medical device 10 or patient 12 through telemetry communication with implantable medical device 10 using transcutaneous electromagnetic signals between telemetry antenna 30 of external device 22 and telemetry antenna 24 of implantable medical device.

External device 22 also contains charging module 32 which is coupled to charging antenna 34 and is adapted to transmit electromagnetic energy to power source 20 of implantable medical device 10 through power antenna 26. Such transcutaneous electromagnetic energy transfer is conventional and well known in the art.

It is to be noted that while external device 22 is shown as containing both control module 28 and charging module 32, it is to be recognized and understood that the control and/or programming functions and energy transfer function of external device 22 could be implemented in separate and independent devices.

Figure 2:
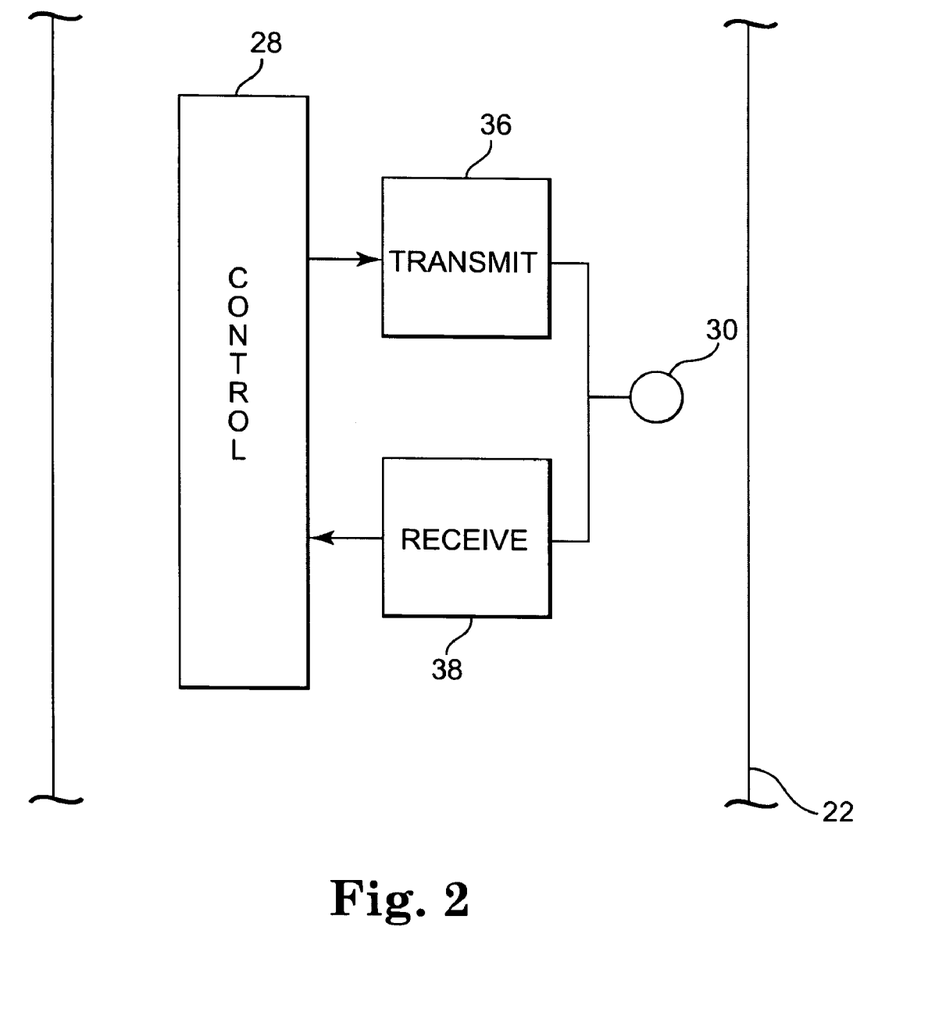
FIG. 2 is a more detailed block diagram of a portion of the external device.

FIG. 2 illustrates a partial block diagram view of external device 22 showing control module 28 and telemetry antenna 30. Control module 28 operates to communicate bi-directionally with implantable medical device 10 through transmit module 36 and receive module 38. Transmit module 36 is responsible for providing data and communication formatting for communication from external device 22 to implantable medical device 10. Receive module 38 is responsible for decoding transmitted information received from implantable medical device 10. Transmit module 36 and receive module 38 are illustrated coupled to a single telemetry antenna 30. It is to be recognized and understood that transmit module 36 and receive module 38 may utilize a common telemetry antenna 30 or may utilize separate and independent antennas.

Figure 3:
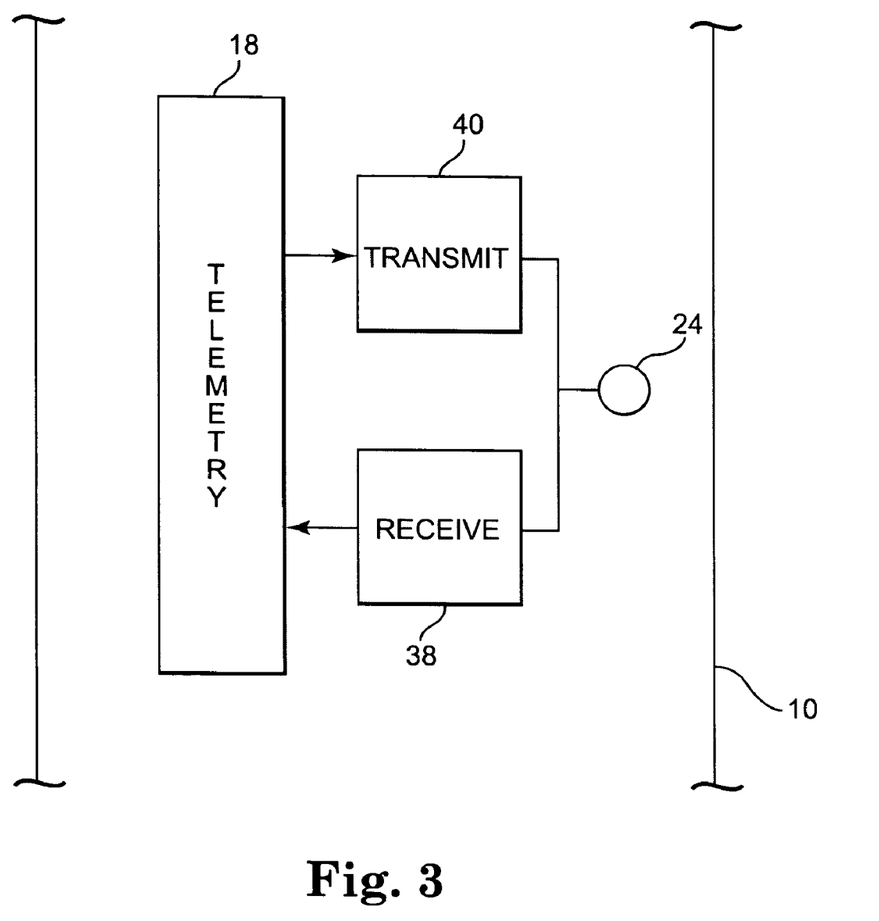
FIG. 3 is a more detailed block diagram of a portion of the implantable medical device.

FIG. 3 illustrates a partial block diagram view of implantable medical device 10 showing telemetry module 18 and telemetry antenna 24. Telemetry module 18 operates to communicate bi-directionally with external device 22 through transmit module 40 and receive module 42. Transmit module 40 is responsible for providing data and communication formatting for communication from implantable medical device 10 to external device 22. Receive module 42 is responsible for decoding transmitted information received from external device 22. Transmit module 40 and receive module 42 are illustrated coupled to a single telemetry antenna 24. It is to be recognized and understood that transmit module 40 and receive module 42 may utilize a common telemetry antenna 24 or may utilize separate and independent antennas.

Implantable medical device 10 may generate significant electromagnetic energy in its normal operation. Such electromagnetic energy may be generated, for example, in the provision of an electrical stimulus pulse or signal train in a neurostimulator. Even drug pumps may produce significant electromagnetic energy in the provision of a medicant to patient 12 since such devices may employ an electrically operated motor or pump which may produce electromagnetic signal or noise spikes during their operation. Alternatively or in addition, substantial electromagnetic is associated with the provision of transcutaneous energy transfer to either supply power to implantable medical device 10 or to recharge power source 20.

In such situations, electromagnetic noise may drown out telemetry signals passing either from external device 22 to implantable medical device 10 or vice versa. Implantable medical device 10 employs receive module 42 adapted to enable to receipt of intelligible telemetry information from external device 22 even while implantable medical device 10 is generating significant electromagnetic signals through the provision of therapeutic output 16, e.g., an electrical stimulus or noise associated with a drug pump, or while implantable medical device 10 is receiving electromagnetic energy from charging module of external device 22.

Capacitors 44 and 46 (see FIG. 4) are center grounded and coupled to receiving coil 48. Zener diode 50, capacitor 52 and resistor 54 along with center grounded capacitors 44 and 46 provide a floating reference level around which telemetry signals appearing at receiving coil 48 may be detected. Receive module 42 operates to produce a digital "one" provided that the amplitude of the oscillating telemetry signal appearing on center-grounded receiving coil 48 are above a predetermined level of the floating reference level.

Figure 4:
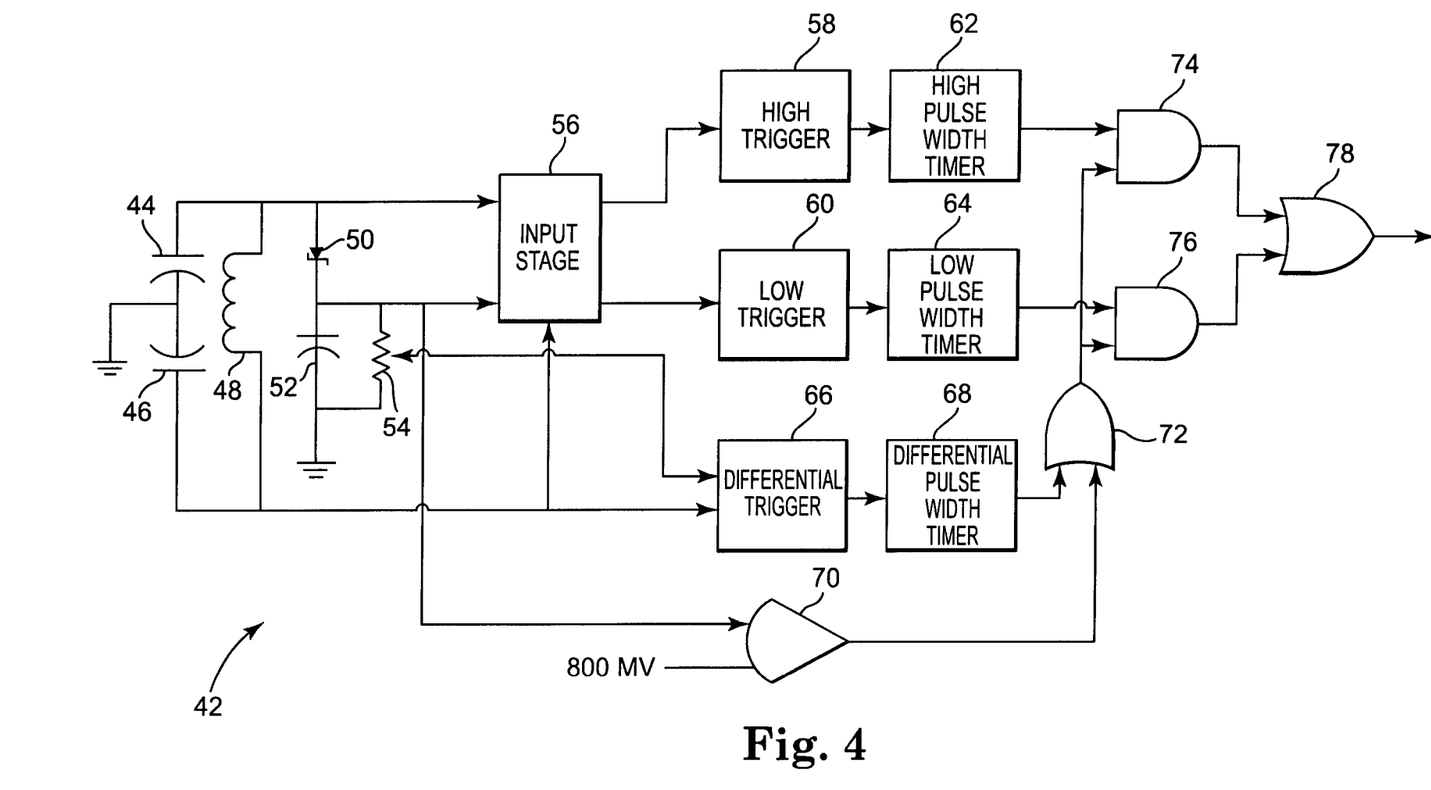
FIG. 4 is a schematic diagram of the receive module in implantable medical device.

Input stage 56 provides a common mode amplifier feeding both high trigger circuit 58 and low trigger circuit 60. High trigger circuit 58 is fed to a high pulse width timer 62 to provide a known minimum pulse width output from high trigger circuit 58. Low pulse width timer circuit 64 similarly provides a known minimum pulse output from low trigger circuit 60.

Dual high and low trigger circuits 58 and 60 provide a dual channel threshold detector.

Receive module 42 also contains differential amplifier 66 providing a differential output from receiving coil 48 adjustable from adjustable resistor 54. Differential pulse width timer 68 provides a known pulse minimum width output from differential amplifier 66.

Common mode amplifier 70 is referenced to a constant voltage, in this case 800 millivolts.

The output of common mode amplifier 70 is "ORed" with the output from differential pulse width timer 68 in OR gate 72. In other words, OR gate 72 passes a high signal whenever either the output from common mode amplifier 70 or differential pulse width timer 68 is high.

The output of each of high pulse width timer 62 and low pulse width timer 64 is "ANDed" with the output from OR gate 72 in AND gates 74 and 76, respectively. In other words, the output from AND gate 74 is high whenever the outputs from both high pulse width timer 62 and OR gate 72 is high. Similarly, the output from AND gate 76 is high whenever the outputs from both low pulse width timer 64 and OR gate 72 is high.

The outputs of OR gates 74 and 76 are "ORed" in OR gate 78. The result is that receive module 42 passes a high signal whenever the output of either high trigger circuit 58 or low trigger circuit 60 is if either the output of differential trigger 66 or common mode amplifier is high.

Figure 5:
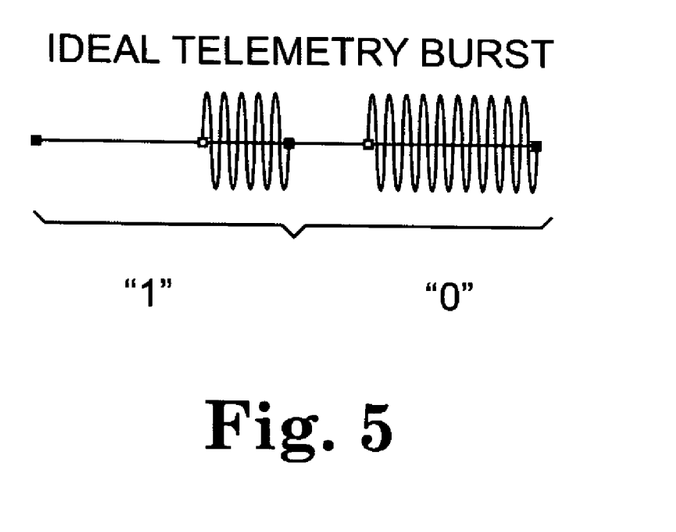
FIG. 5 shows an ideal telemetry burst.

In a preferred embodiment, the telemetry signal broadcast by the external device 22 has a base band of 4.4 kilobits per second and a carrier frequency of 175 kiloHertz. The telemetry signal is amplitude modulated. One's and zero's are communicated using a psuedo-AM (amplitude modulation) communication scheme where the length of each pulse and the time in between pulses determines if the pulse represents a 1 or a 0. FIG. 5 shows an ideal Telemetry N burst with the 1's and the 0's labeled to show timing differences between the two.

Figure 6:
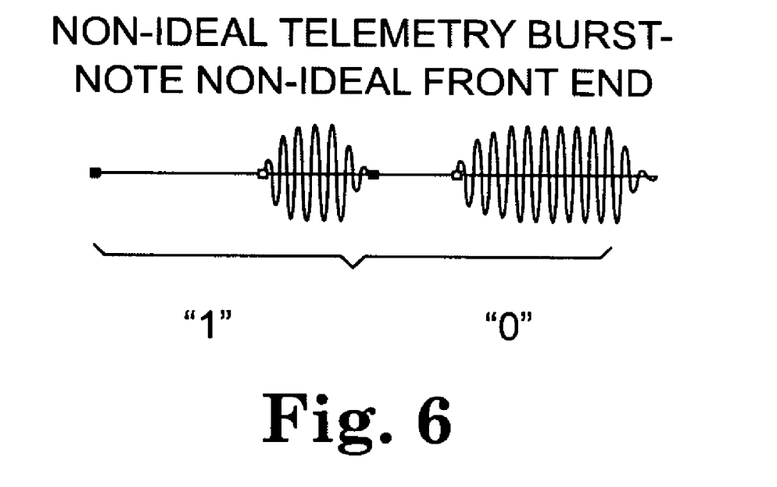
FIG. 6 shows an non-ideal telemetry burst.

The external device 22, however, may not produce an ideal telemetry burst. A non-ideal telemetry burst may have a rise time where the beginning cycles do not reach full amplitude for a certain amount of time. FIG. 6 shows an example of a non-ideal telemetry burst.

Receive module 42 provides peak tracking and dynamic threshold control. The first function is tracking the peak of the received telemetry signal. A RC time constant is set to hold this peak value for a certain amount of time in between bursts and after the end-of-message signal. The second function is to set the dynamic threshold. This is accomplished by taking a certain percentage of the peak voltage (determined by the peak tracking function) and sending it on, in the form of an offset, to the trigger circuits 58 and 60.

The peak of the received telemetry signal is tracked using the peak tracker. The peak voltage is set-up on the hybrid capacitors 44 and 46. A time constant is involved in setting up the peak voltage because of the RC time constant.

Figure 7:
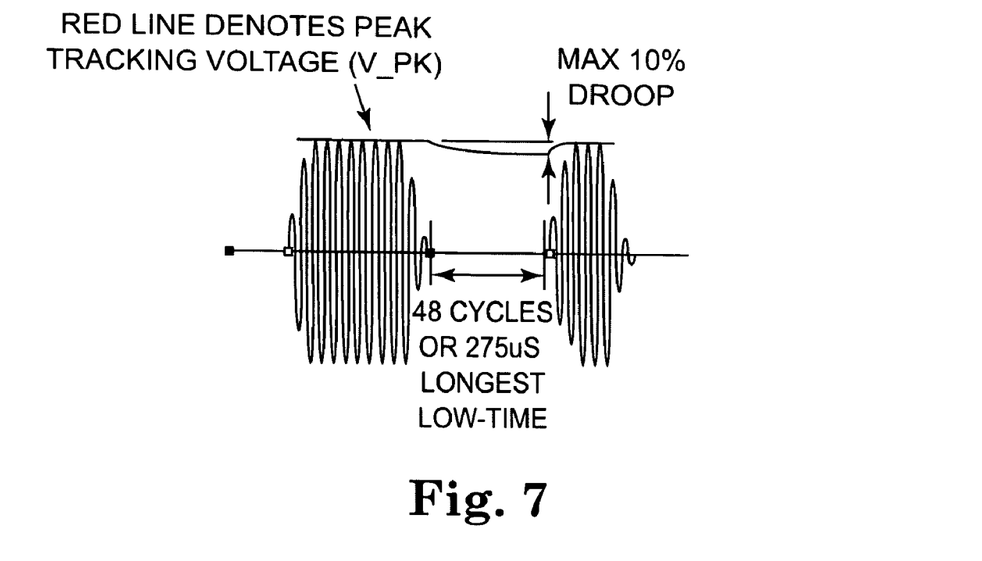
FIG. 7 illustrates in between burst peak tracker operation.

The peak tracker is designed to hold the dynamic threshold to a certain percentage of the peak voltage in between bursts. It is the intent of the peak tracker to only let the peak voltage set on the capacitor drop 10% in between bursts. The worst-case ~2 millisecond time constant allows the peak tracker to only lose 10% of the peak value during the longest low-time of the message. FIG. 7 illustrates in between burst peak tracker operation.

The longest low-time in a message is 48 cycles, or 275 microseconds, just before the 16 cycle end-of-message burst. If we again look to the equation $$0.9\ V_0 = V_0 e^{\frac{-275uS}{\tau}}$$

and set V to 90% of $V_O$ and set the time to be 275 microseconds we can solve for the time constant needed to keep the peak tracker at 90% of the peak signal in between bursts.

After the message is finished the voltage on capacitors 44 and 46 will clear according to the time constant as well. The capacitors 44 and 46 will be defined as cleared once it has decayed down to 10% of its original value.

Figure 8:
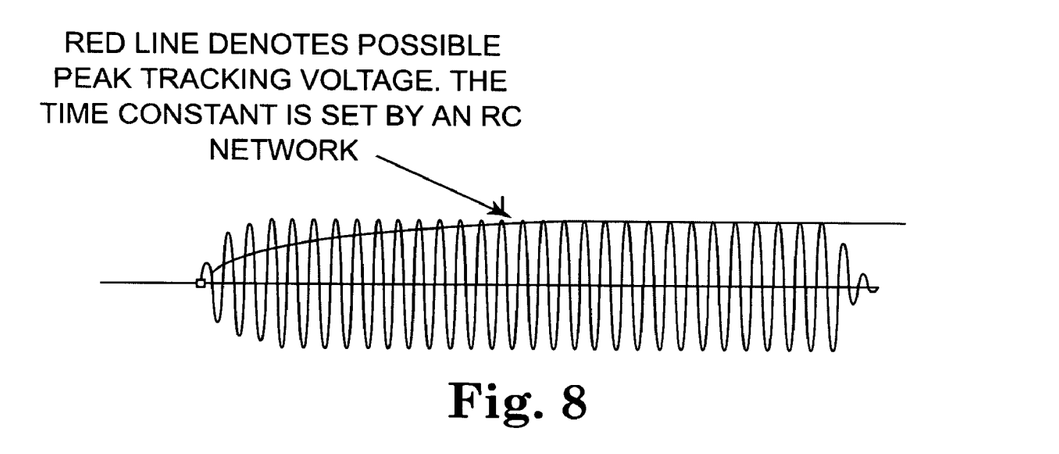
FIG. 8 illustrates a peak tracking signal on a telemetry burst.

FIG. 8 shows a reasonable telemetry burst with an exponentially rising peak tracking signal.

The dynamic threshold control uses the voltage created by the peak voltage detector and takes some percentage of that voltage. The percentage of the peak voltage is used as the new receiver threshold during a message. The dynamic threshold allows communication in a noisy environment by increasing the detection threshold when there is sufficient signal on the coil.

The design has the option of changing the percentage of the peak received voltage that the dynamic threshold will rise to is adjustable resistor 54.

Figure 9:
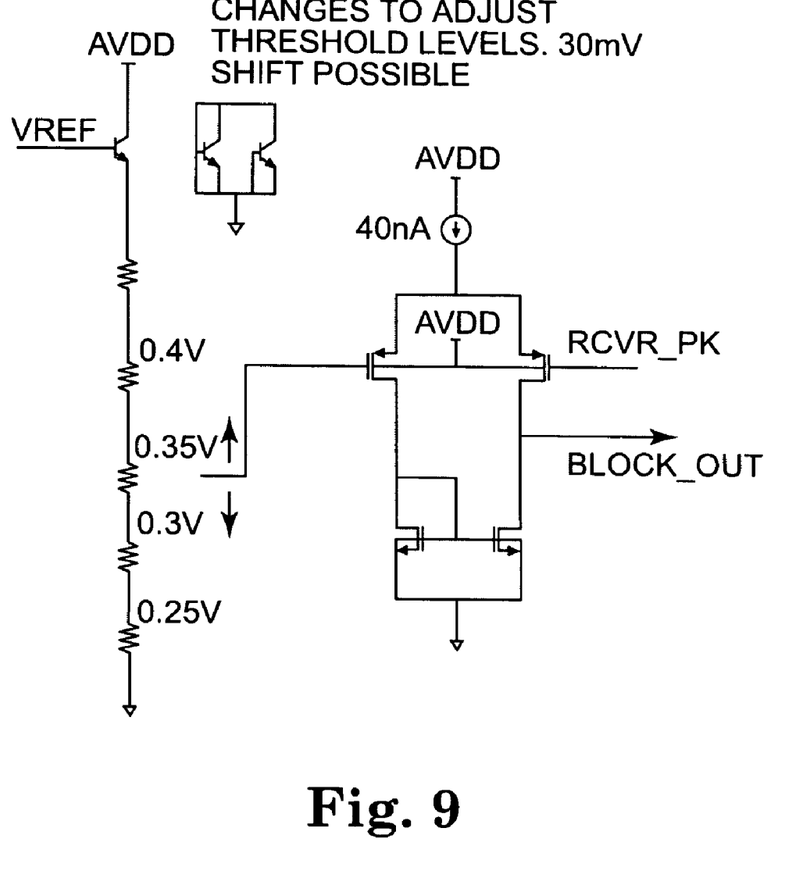
FIG. 9 is a fixed threshold control block circuit diagram.

The fixed threshold control block controls the fixed threshold level. This block uses the peak of the signal measured using the peak signal from the peak detector and dynamic threshold control block and compares it to a fixed threshold level set for a specific device. If the peak of the signal is larger than the fixed threshold level the receiver's comparator block is activated using a signal. If the peak signal is smaller than the fixed threshold level of the receiver the comparator block is de-activated.

FIG. 9 shows that the fixed threshold level is realized by sending a current through a resistor and measuring the voltage across that resistor. This voltage is then compared to the peak voltage measured in the peak tracker and dynamic threshold control.

As noted in the purpose statement, receive module 42 senses and conditions the telemetry antenna voltage received at the physical layer and creates a digital signal that represents the telemetry signal at the data-link layer. Receive module 42 also provides the signal-to-noise ratio necessary to maintain operation during stimulation.

A peak tracker tracks the peak of the antenna voltage across Zener diode 50. A time constant sets the growth and decay properties of the peak voltage as compared to the telemetry (or noise) burst. The voltage created using the RC is considered the peak of the telemetry burst. This peak voltage is then used in the fixed threshold to determine if the telemetry burst is above the fixed threshold. The peak voltage is also used to set the dynamic threshold.

The peak tracker block also provides a bias for input stage 56.

Input stage 56 acts as a pre-amplifier with non-linear compression and gain for the high and low signal paths of the receive module 42. Input stage 56 amplifies the differential and filters the common mode signal between both sides of the antenna. These amplified signals are both sent directly to the high and low trigger circuits (58 and 60) for further processing. When the signal level is greater, the signal is sent to the low channel trigger circuit 60. When the signal level is less, the signal is sent to the high channel trigger circuit 58.

Input stage 56 also provides a band pass function.

Common mode amplifier 70 provides a fixed threshold control ensuring that a signal below the fixed threshold does not cause the receive module 42 to trip. The fixed threshold control uses a comparator 70 to compare the peak voltage of the received signal from the peak tracker to the fixed threshold voltage (800 millivolts). If the peak voltage of the received signal is larger than the fixed threshold level comparator 70 will be activated. If the peak of the received signal is smaller than the fixed threshold level the comparator 70 will be de-activated.

High and low trigger circuits 58 and 60 are identical and are basically Schmitt triggers that trigger when one input goes negative or positive relative to the other input. The high and low trigger circuits are then able to create a digital signal that should represent the carrier frequency of 175 kiloHertz.

Figure 10:
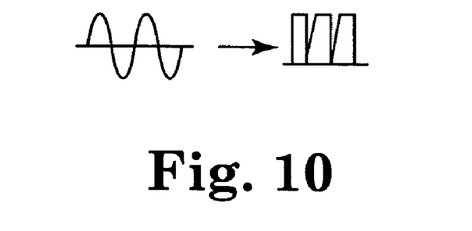
FIG. 10 illustrates a trigger signal flow diagram.

The basic signal flow is shown in FIG. 10.

The differential noise trigger 66 provides a dynamic threshold to filter out low-level noise when the signal level is large enough.

Figure 11:
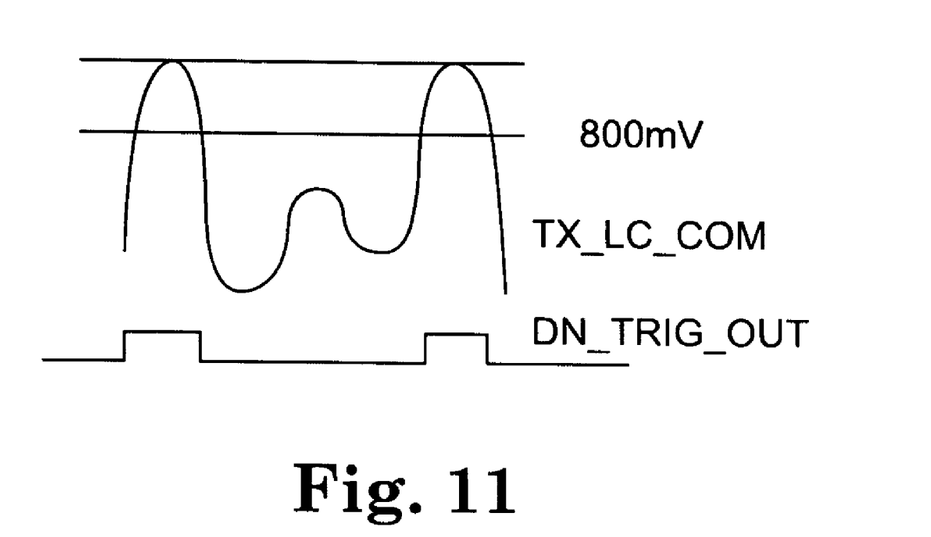
FIG. 11 illustrates differential trigger operation.

FIG. 11 shows how the differential noise trigger 66 ignores the low-level noise when the signal level seen on receive coil 48 is large enough.

The high and low pulse-width timers (62 and 64) are identical and perform the same function for their respective signal paths. They are re-triggerable time-out timers that use the output of the triggers (high and low respectively.)

The pulse-width timers (62 and 64) effectively filter out the carrier frequency of 175 kiloHertz and create a 4.4 kilobits per second signal. The timers accomplish this by looking for the input signal to go high (2 volts) and setting a timer. As soon as the input signal goes high the timer is set and the output signal goes high. If the input signal is high when the timer has expired the timer will reset and the output signal will remain high. If the input signal is low when the timer expires the output signal will go low.

Figure 12:
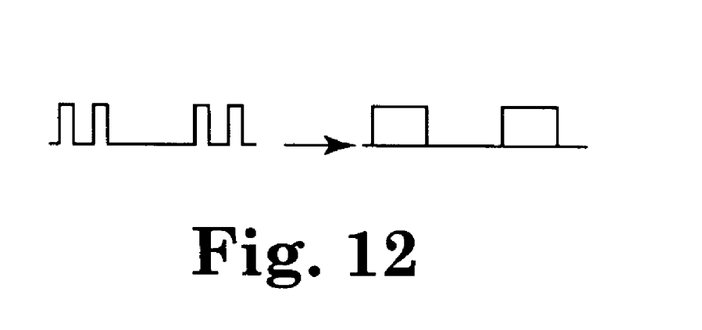
FIG. 12 illustrates a pulse width timer signal flow diagram.

FIG. 12 shows the signal flow of the pulse width timers 62 and 64. The signal from the triggers is taken and the pulse-width timer creates the 4.4 kilobit per second signal.

Differential pulse width timer 68 performs the same function for differential trigger 66 as the high and low pulse width timers (62 and 64) do for high and low triggers (58 and 60) and is also re-triggerable.

Differential trigger 66 acts as a switch to turn on the differential noise filtering. Differential trigger 66 compares a percentage of the voltage of the received signal across receive coil 48 to a predetermined voltage level. When the received voltage is larger than a predetermined voltage value, differential filtering is enabled. Differential filtering filters out low-level noise when there is a large amplitude on the received telemetry signal.

After a transmission has occurred, the capacitor on the peak tracker should be cleared. If the capacitor is not cleared, the receive module 42 could ignore a telemetry downlink because the dynamic threshold would be set high because of a voltage on the peak tracker capacitor. The capacitor is shorted when the transmitter is inactive and the receiver is active.

Uplink telemetry communication is achieved by utilizing transmit module 40 in implantable medical device 10 and receive module 38 in external device 22. Transmit module 40 is conventional in nature and well known in the art using conventional techniques.

Figure 13:
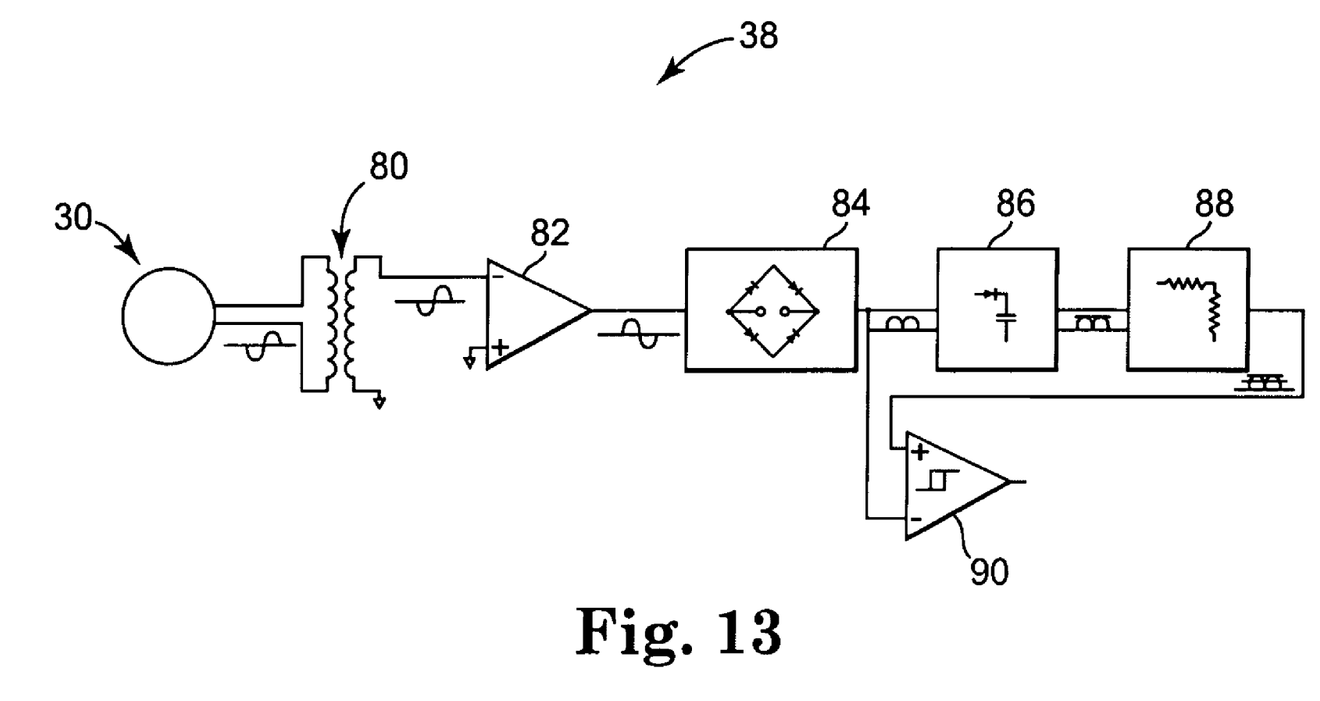
FIG. 13 is a schematic block diagram of a receive module in an external device.

Receive module 38 in external device 22 is much more straight forward than receive module 42 in implantable medical device. Telemetry antenna 30 is coupled directly to transformer 80. The signal from transformer 80 is amplified in amplifier 82 and full wave rectified in full wave rectifier 84. Peak detector 86 uses a series diode and a parallel capacitor to detect a peak value. A threshold is established is threshold block 88 consisting of a voltage divider. Comparator 90 compares the signal from full wave rectifier 84 and the signal from the threshold block 88 to produce a positive output when the full wave rectified signal is above the threshold signal.

Operation of any circuitry in implantable medical device consumes power. Since size and longevity are usually primary concerns for implantable medical devices, any power savings can yield either size or longevity improvements or both. The telemetry module 18 as well as transmit module 40 and receive module 42 consume power in implantable medical device 10. This is particularly true since many components contained in the transmit and receive modules 40 and 42 are analog components and, as such, may require voltages and currents in excess of that typically required by digital components.

Figure 14:
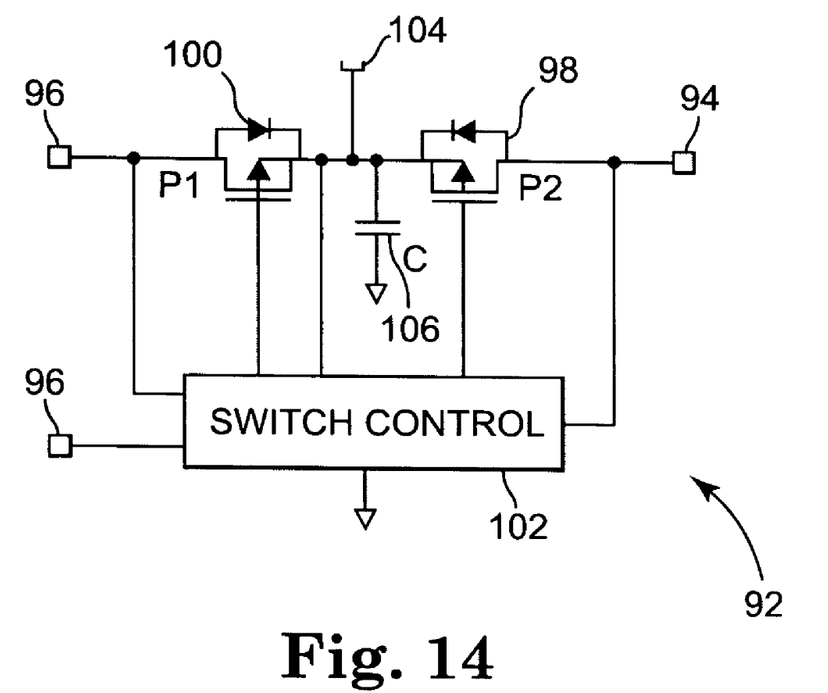
FIG. 14 is a schematic diagram is a power supply switched voltage circuit.

Switched supply block 92 provides power to one or more of telemetry module 18, transmit module 40 and/or receive module 42 from the telemetry signal when implantable medical device 10 is receiving a telemetry signal. Switched supply block 92 provides power to circuits that need a high-voltage power supply when high voltage levels are seen on telemetry antenna 24 while receiving a telemetry transmission. Switched supply block 92 illustrated in FIG. 14 is a two-FET well-switcher that places the voltage from either the internal power source or switched supply from the telemetry antenna depending on which one is larger. Peripheral circuitry has been added to the well-switcher to ensure proper operation under all system conditions.

Switched supply block 92 is a well switcher that chooses the higher of the two voltages to supply a number of circuits in receive module 42. Switched supply block 92 allows the receive module 42 to use the energy on the receive coil 48 to power the receive module 42 during telemetry reception when the received signal amplitude creates a voltage that is larger than the internal power source voltage.

Switched supply block 92 has hysteresis around 4.0 volts. When the voltage on receive coil 48 is increasing the switched supply block 92 will begin using this voltage as a supply voltage as soon as it is greater than the voltage of the internal power source.

Voltage 94 from the internal power source is available to switched supply block 92. Also available is voltage 96 from receive coil 48. Voltage 94 from the internal power source of implantable medical device 10 is fed to field effect transistor (FET) 98 while voltage 96 from receive coil 48 is fed to field effect transistor (FET) 100. Switch control logic 102 is coupled to both voltages 94 and 96 and controls FETs 98 and 100 to effectively switch between voltage sources depending upon which voltage source is higher. The switched supply block 92 output voltage 104 is taken from the outputs of both FETs 98 and 100 and stabilized with capacitor 106.

The contents of provisional U.S. Application Ser. No. 60/589,393, filed Jul. 20, 2004, and provisional U.S. Application Ser. No. 60/589,950, filed Jul. 21, 2004, are hereby incorporated by reference.

Thus, embodiments of the concurrent delivery of treatment therapy with telemetry in an implantable medical device are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device for providing a therapeutic output to a patient and being configured for transcutaneous telemetry communication with an external device via a telemetry signal, comprising;
   an internal power source;
   an electronics module adapted to supply said therapeutic output to said patient;
   a telemetry module configured for said transcutaneous telemetry communication; and
   said telemetry module obtaining power to operate said telemetry module from said telemetry signal during transcutaneous telemetry communication.

2. An implantable medical device as in claim 1 wherein said telemetry module relies upon power from said telemetry signal to supplement power from said internal power source.

3. An implantable medical device as in claim 1 wherein telemetry module obtains power from one of said internal power source and said telemetry signal.

4. An implantable medical device as in claim 1 wherein said telemetry module obtains power from said telemetry signal instead of from said internal power source when said telemetry signal is available.

5. An implantable medical device as in claim 4 wherein said telemetry module always obtains power from said telemetry signal instead of from said internal power source whenever said telemetry signal is available.

6. An implantable medical device as in claim 1 wherein said telemetry module obtains power from said telemetry signal whenever energy from said telemetry signal is sufficient to power said telemetry module.

7. An implantable medical device as in claim 6 wherein said telemetry module obtains power from said telemetry signal instead of said internal power source whenever energy from said telemetry signal is sufficient to power said telemetry module.

8. A system for providing a therapeutic output to a patient, comprising;
   an external device configured for transcutaneous telemetry communication with said implantable medical device; and
   said implantable medical device as in claim 1.

9. An implantable medical device for providing a therapeutic output to a patient, configured for transcutaneous telemetry communication with an external device, comprising;
   an internal power source;
   an electronics module adapted to supply said therapeutic output to said patient;
   a telemetry module configured for transcutaneous telemetry communication using a telemetry signal; and
   a switching module, operatively coupled to said power source and said telemetry module, providing power to operate said telemetry module from said telemetry signal when said telemetry signal is available.

10. An implantable medical device as in claim 9 wherein said telemetry module relies upon power from said telemetry signal to supplement power from said internal power source.

11. An implantable medical device as in claim 9 wherein said switching module supplies power to said telemetry module from one of said internal power source and said telemetry signal.

12. An implantable medical device as in claim 9 wherein said switching module supplies power to said telemetry module from telemetry signal instead of from said internal power source when said telemetry signal is available.

13. An implantable medical device as in claim 12 wherein said switching module always supplies power to said telemetry module from said telemetry signal instead of from said internal power source whenever said telemetry signal is available.

14. An implantable medical device as in claim 9 wherein said switching module supplies power to said telemetry module from said telemetry signal whenever power from said telemetry signal is sufficient to power said telemetry module.

15. An implantable medical device as in claim 14 wherein switching module supplies power to said telemetry module from said telemetry signal instead of from said internal power source whenever energy from said telemetry signal is sufficient to power said telemetry module.

16. A system for providing a therapeutic output to a patient, comprising;
   an external device configured for transcutaneous telemetry communication with said implantable medical device; and
   said implantable medical device as in claim 9.

17. A method of providing transcutaneous telemetry communication with an implanted medical device having an internal power source, comprising the steps of:
   providing said transcutaneous telemetry communication with a telemetry module of said implanted medical device using a telemetry signal;
   supplying power to said telemetry module in said implanted medical device with said internal power source when said telemetry signal is not available; and
   supplying power to said telemetry module in said implanted medical device with said telemetry signal to operate said telemetry module when said telemetry signal is available.

18. A method of providing transcutaneous telemetry communication with an implanted medical device having an internal power source, comprising the steps of:
- providing said transcutaneous telemetry communication with a telemetry module of said implanted medical device using a telemetry signal;
- supplying power to said telemetry module in said implanted medical device with said internal power source when said telemetry signal is not available; and
- supplying power to said telemetry module in said implanted medical device with said telemetry signal to operate said telemetry module when said telemetry signal is available;
- wherein said supplying power to said telemetry module in said implanted medical device with said telemetry signal step supplements power from said internal power source.

19. A method as in claim 18 wherein said supplying power to said telemetry module in said implanted medical device with said telemetry signal step replaces power from said internal power source.

20. A method as in claim 18 wherein said supplying power to said telemetry module in said implanted medical device with said telemetry signal step is always accomplished whenever said telemetry signal is available.

21. A method as in claim 18 wherein said supplying power to said telemetry module in said implanted medical device with said telemetry signal step is accomplished whenever energy from said telemetry signal is sufficient to power said telemetry module.

22. A method as in claim 21 wherein said supplying power to said telemetry module in said implanted medical device with said telemetry signal step is accomplished instead of said supplying power to said telemetry module in said implanted medical device with said internal power source step whenever energy from said telemetry signal is sufficient to power said telemetry module.

23. An implantable medical device for providing a therapeutic output to a patient and being configured for transcutaneous telemetry communication with an external device via a telemetry signal, comprising;
- a power antenna;
- an internal battery operatively coupled to said power antenna and adapted to obtain power from said power antenna;
- an electronics module operatively coupled to receive power from said internal battery, said electronics module adapted to supply said therapeutic output to said patient;
- a telemetry antenna; and
- a telemetry module operatively coupled to said telemetry antenna and configured for said transcutaneous telemetry communication;
- said telemetry module obtaining power to operate said telemetry module from said telemetry signal during transcutaneous telemetry communication.

24. An implantable medical device as in claim 23 wherein said telemetry module relies upon power from said telemetry signal to supplement power from said internal battery.

25. An implantable medical device as in claim 23 wherein said telemetry module obtains power from one of said internal battery and said telemetry signal.

26. An implantable medical device as in claim 23 wherein said telemetry module obtains power from said telemetry signal instead of from said internal battery when said telemetry signal is available.

27. An implantable medical device as in claim 26 wherein said telemetry module always obtains power from said telemetry signal instead of from said internal battery whenever said telemetry signal is available.

28. An implantable medical device as in claim 23 wherein said telemetry module obtains power from said telemetry signal whenever energy from said telemetry signal is sufficient to power said telemetry module.

29. An implantable medical device as in claim 28 wherein said telemetry module obtains power from said telemetry signal instead of said internal battery whenever energy from said telemetry signal is sufficient to power said telemetry module.

30. An implantable medical device as in claim 23 wherein said transcutaneous telemetry communication is bi-directional.

31. A system for providing a therapeutic output to a patient, comprising;
- an external device configured for transcutaneous telemetry communication with said implantable medical device; and
- said implantable medical device as in claim 23.

32. An implantable medical device for providing a therapeutic output to a patient, configured for transcutaneous telemetry communication with an external device, comprising;
- a power antenna;
- an internal battery operatively coupled to said power antenna and adapted to obtain power from said power antenna;
- an electronics module operatively coupled to receive power from said internal battery, said electronics module adapted to supply said therapeutic output to said patient;
- a telemetry antenna;
- a telemetry module operatively coupled to said telemetry antenna and configured for transcutaneous telemetry communication using a telemetry signal; and
- a switching module, operatively coupled to said battery and said telemetry module, providing power to operate said telemetry module from said telemetry signal when said telemetry signal is available.

33. An implantable medical device as in claim 32 wherein said telemetry module relies upon power from said telemetry signal to supplement power from said internal battery.

34. An implantable medical device as in claim 32 wherein said switching module supplies power to said telemetry module from one of said internal battery and said telemetry signal.

35. An implantable medical device as in claim 32 wherein said switching module supplies power to said telemetry module from telemetry signal instead of from said internal battery when said telemetry signal is available.

36. An implantable medical device as in claim 35 wherein said switching module always supplies power to said telemetry module from said telemetry signal instead of from said internal battery whenever said telemetry signal is available.

37. An implantable medical device as in claim 32 wherein said switching module supplies power to said telemetry module from said telemetry signal whenever power from said telemetry signal is sufficient to power said telemetry module.

38. An implantable medical device as in claim 37 wherein said switching module supplies power to said telemetry module from said telemetry signal instead of from said internal battery whenever energy from said telemetry signal is sufficient to power said telemetry module.

39. An implantable medical device as in claim 32 wherein said transcutaneous telemetry communication is bi-directional.

40. A system for providing a therapeutic output to a patient, comprising;
an external device configured for transcutaneous telemetry communication with said implantable medical device; and
said implantable medical device as in claim 32.

41. A method of providing transcutaneous telemetry communication with an implanted medical device having an internal battery operatively coupled to a power antenna and a telemetry module operatively coupled to a telemetry antenna, comprising the steps of:
providing power to said internal battery by way of a power signal transmitted to said power antenna;
providing said transcutaneous telemetry communication with said telemetry module of said implanted medical device by way of said telemetry antenna using a telemetry signal;
supplying power to said telemetry module in said implanted medical device with said internal battery when said telemetry signal is not available; and
supplying power to said telemetry module in said implanted medical device with said telemetry signal to operate said telemetry module when said telemetry signal is available.

42. A method as in claim 41 wherein said transcutaneous telemetry communication is bi-directional.

43. A method of providing transcutaneous telemetry communication with an implanted medical device having an internal battery operatively coupled to a power antenna and a telemetry module operatively coupled to a telemetry antenna, comprising the steps of:
providing power to said internal battery by way of a power signal transmitted to said power antenna;
providing said transcutaneous telemetry communication with said telemetry module of said implanted medical device by way of said telemetry antenna using a telemetry signal;
supplying power to said telemetry module in said implanted medical device with said internal battery when said telemetry signal is not available; and
supplying power to said telemetry module in said implanted medical device with said telemetry signal to operate said telemetry module when said telemetry signal is available;
wherein said supplying power to said telemetry module in said implanted medical device with said telemetry signal step supplements power from said internal battery.

44. A method as in claim 43 wherein said supplying power to said telemetry module in said implanted medical device with said telemetry signal step replaces power from said internal battery.

45. A method as in claim 43 wherein said supplying power to said telemetry module in said implanted medical device with said telemetry signal step is always accomplished whenever said telemetry signal is available.

46. A method as in claim 43 wherein said supplying power to said telemetry module in said implanted medical device with said telemetry signal step is accomplished whenever energy from said telemetry signal is sufficient to power said telemetry module.

47. A method as in claim 46 wherein said supplying power to said telemetry module in said implanted medical device with said telemetry signal step is accomplished instead of said supplying power to said telemetry module in said implanted medical device with said internal battery step whenever energy from said telemetry signal is sufficient to power said telemetry module.

48. A method as in claim 43 wherein said transcutaneous telemetry communication is bi-directional.

\* \* \* \* \*